US00PP18928P2

(12) United States Plant Patent
Jepsen

(10) Patent No.: US PP18,928 P2
(45) Date of Patent: Jun. 10, 2008

(54) ***KALANCHOE* PLANT NAMED 'SARAH'**

(50) Latin Name: *Kalanchoe blossfeldiana*
Varietal Denomination: Sarah

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 11/633,112

(22) Filed: Dec. 1, 2006

(51) Int. Cl.
*A01H 5/00* (2006.01)

(52) U.S. Cl. ..... Plt./335

(58) Field of Classification Search ..... Plt./335
See application file for complete search history.

*Primary Examiner*—Anne Marie Grunberg
*Assistant Examiner*—Louanne Krawczewicz Myers
(74) *Attorney, Agent, or Firm*—C. A. Whealy

(57) ABSTRACT

A new and distinct cultivar of *Kalanchoe* plant named 'Sarah', characterized by its upright, uniform and moderately vigorous growth habit; dark green-colored leaves; uniform, freely and early flowering habit; large orange red-colored flowers; and excellent postproduction longevity.

1 Drawing Sheet

Botanical designation: *Kalanchoe blossfeldiana.*
Cultivar denomination: 'Sarah'.

BACKGROUND OF THE INVENTION

The present invention relates to a new and distinct cultivar of *Kalanchoe,* botanically known as *Kalanchoe blossfeldiana,* and hereinafter referred to by the name 'Sarah'.

The new *Kalanchoe* is a product of a planned breeding program conducted by the Inventor in Hinnerup. Denmark. The objective of the breeding program is to create new *Kalanchoe* cultivars with attractive foliage and flower coloration.

The new *Kalanchoe* originated from a cross-pollination made by the Inventor in Hinnerup, Denmark in June, 2004, of the *Kalanchoe blossfeldiana* cultivar Celine, disclosed in U.S. Plant patent application Ser. No. 10/654,563, as the female, or seed parent with a proprietary selection of *Kalanchoe blossfeldiana* identified as code number KJ 2003 0936, not patented, as the male, or pollen, parent. The cultivar Sarah was discovered and selected by the Inventor as a flowering plant from within the progeny of the stated cross-pollination in a controlled environment in Hinnerup, Denmark in March, 2005.

Asexual reproduction of the new *Kalanchoe* by vegetative terminal cuttings in a controlled environment in Hinnerup, Denmark since July, 2005, has shown that the unique features of this new *Kalanchoe* are stable and reproduced true to type in successive generations.

SUMMARY OF THE INVENTION

The cultivar Sarah has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sarah'.

These characteristics in combination distinguish 'Sarah' as a new and distinct cultivar of *Kalanchoe:*

1. Upright, uniform and moderately vigorous growth habit.
2. Dark green-colored leaves.
3. Uniform, freely and early flowering habit.
4. Large orange red-colored flowers.
5. Excellent postproduction longevity.

Plants of the new *Kalanchoe* can be compared to plants of the female parent, the cultivar Celine. Plants of the new *Kalanchoe* differ primarily from plants of the cultivar Celine in flower color as plants of the cultivar Celine have yellow orange-colored flowers.

Plants of the new *Kalanchoe* can also be compared to plants of the male parent selection. Plants of the new *Kalanchoe* differ from plants of the male parent selection primarily in plant size and flower color.

Plants of the new *Kalanchoe* can be compared to plants of the *Kalanchoe blossfeldiana* cultivar Carmen, disclosed in U.S. Plant Pat. No. 15,838. In side-by-side comparisons conducted in Hinnerup, Denmark, plants of the new *Kalanchoe* differed from plants of the cultivar Carmen in the following characteristics:

1. Plants of the new *Kalanchoe* were slightly larger than plants of the cultivar Carmen.
2. Flowers of plants of the new *Kalanchoe* had smaller leaves and flowers than plants of the cultivar Carmen.
3. Plants of the new *Kalanchoe* were more freely flowering than plants of the cultivar Carmen.
4. Plants of the new *Kalanchoe* and the cultivar Carmen differed in flower color.
5. Plants of the new *Kalanchoe* flowered about six days later than plants of the cultivar Carmen.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*.

The photograph at the top of the sheet comprises a side perspective view of a typical flowering plant of 'Sarah' grown in a container.

The photograph at the bottom of the sheet comprises a top perspective view of a typical flowering plant of 'Sarah' grown in a container.

DETAILED BOTANICAL DESCRIPTION

The aforementioned photographs and following observations, measurements and values describe plants grown in Hinnerup, Denmark in a glass-covered greenhouse during the winter and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about 13 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Sarah.

Parentage:

*Female, or seed, parent.*—*Kalanchoe blossfeldiana* cultivar Celine, disclosed in U.S. Plant patent application Ser. No. 10/654,563.

*Male or pollen parent.*—Proprietary selection of *Kalanchoe blossfeldiana* identified as code number KJ 2003 0936, not patented.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About 21 days at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 6-cm to 10-cm containers.

*Plant height at flowering.*—About 20 cm to 27 cm.

*Plant diameter at flowering.*—About 22 cm.

*Branching habit.*—Usually about two to five lateral branches develop per plant. Pinching (removal of the terminal apex) is not required but will enhance lateral branch development.

Lateral branch description:

*Length.*—About 15 cm.

*Diameter.*—About 4 mm.

*Internode length.*—About 2 cm to 4 cm.

*Aspect.*—Erect.

*Strength.*—Strong.

*Texture.*—Smooth, glabrous.

*Color.*—147B.

Foliage description:

*Arrangement.*—Opposite, simple; generally symmetrical.

*Quantity of leaves per lateral branch.*—About 4.

*Length, vegetative plants.*—About 8 cm to 11 cm.

*Width, vegetative plants.*—About 3 cm to 11 cm.

*Length, generative plants.*—About 5 cm to 6 cm.

*Width, generative plants.*—About 2 cm to 6 cm.

*Shape.*—Ovate.

*Apex.*—Obtuse to mucronate.

*Base.*—Cuneate.

*Margin.*—Serrate; undulate.

*Texture, upper and lower surfaces.*—Glabrous, leathery; succulent.

*Venation pattern.*—Pinnate.

*Color.*—Developing foliage, upper surface: 137B. Developing foliage, lower surface: 137C. Fully developed foliage, upper surface: 147A; venation, 146B. Fully developed foliage, lower surface: 146A; venation, 146B.

*Petiole.*—Length: About 5 mm to 10 mm. Diameter: About 5 mm to 6 mm. Texture, upper and lower surfaces: Smooth, glabrous. Color, upper and lower surfaces: 137C.

Flower description:

*Flower arrangement and habit.*—Single flowers arranged singly in compound dichasial cymes that arise from leaf axils. Uniform and freely flowering habit with usually about 40 to 80 flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Early flowering habit; under short day/long night photoinductive conditions, about 74 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 4 cm to 10 cm.

*Inflorescence diameter.*—About 5 cm to 9 cm.

*Flower diameter.*—About 1.6 cm.

*Flower length (height).*—About 1.8 cm.

*Flower bud.*—Shape: Lanceolate. Length: About 1.3 cm. Diameter: About 3 mm. Color: 26B and N30A.

*Petals.*—Arrangement: About four fused at the base. Length (largest petals): About 1.8 cm. Width (largest petals): About 6 mm. Aspect: Slightly upright to eventually recurved. Shape: Rounded obovate. Apex: Apiculate. Margin: Entire. Texture, upper and lower surfaces: Smooth, glabrous. Color: When opening and fully opened, upper surface: N30B. When opening and fully opened, lower surface: 26C and N30B.

*Sepals.*—Appearance: Four fused at the base. Length: About 9 mm. Width: About 2 mm. Shape: Lanceolate. Apex: Acute. Margin: Entire. Texture, upper and lower surfaces: Smooth; glabrous. Color, immature, upper and lower surfaces: 146D. Color, mature, upper and lower surfaces: 146C.

*Peduncles.*—Length: About 2 mm to 8 mm. Diameter: About 1 mm. Aspect: Erect to perpendicular. Strength: Strong. Texture: Smooth, glabrous. Color: 147B.

*Reproductive organs.*—Androecium: Stamen number: About eight per flower. Anther shape: Elliptic to oblong, flat. Anther size: About 1 mm by 1 mm. Anther color: Close to 22B. Amount of pollen: Moderate. Pollen color: Close to 20A. Gynoecium: Pistil number: About four per flower. Pistil length: About 1.1 cm. Style length: About 2 mm. Style color: N144A. Stigma shape: Rounded. Stigma color: N144A. Ovary color: Close to 144C.

*Seed.*—Quantity of seeds per ovary: About 40. Length: About 1 mm. Diameter: About 0.5 mm. Color: 145B.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoe*.

It is claimed:

1. A new and distinct *Kalanchoe* plant named 'Sarah' as illustrated and described.

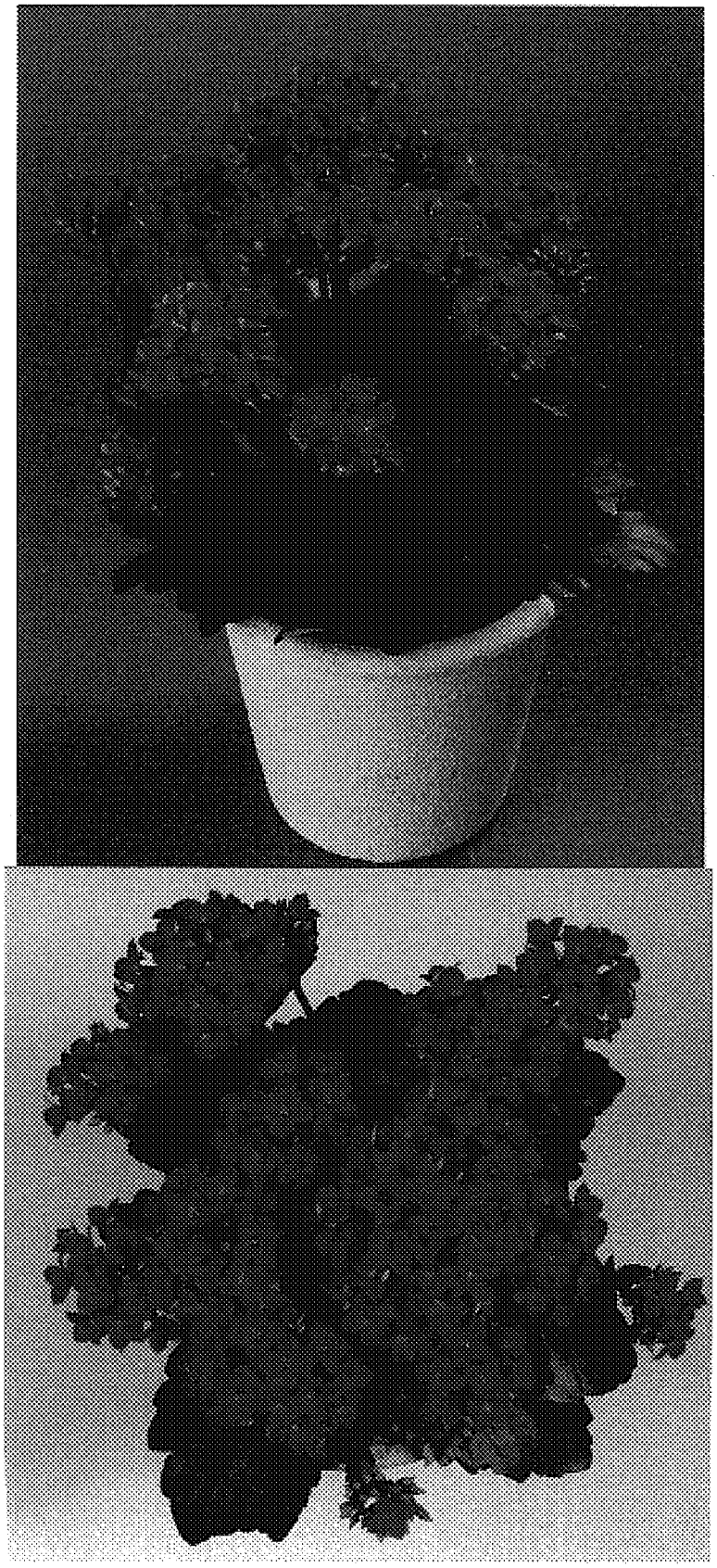

* * * * *